(12) United States Patent
Cassidy et al.

(10) Patent No.: US 8,632,624 B2
(45) Date of Patent: Jan. 21, 2014

(54) FLUID TRAP AND METHOD OF SEPARATING FLUIDS

(75) Inventors: David E. Cassidy, Chelmsford, MA (US); Eric E. May, Norfolk, MA (US); Garrett Austin Sheffer, Hoboken, NJ (US)

(73) Assignee: General Electric Company, Schenectady, NY (US)

( * ) Notice: Subject to any disclaimer, the term of this patent is extended or adjusted under 35 U.S.C. 154(b) by 224 days.

(21) Appl. No.: 13/272,907

(22) Filed: Oct. 13, 2011

(65) Prior Publication Data

US 2013/0092640 A1 Apr. 18, 2013

(51) Int. Cl.
*B01D 19/00* (2006.01)

(52) U.S. Cl.
USPC ............ 95/258; 95/262; 95/260; 95/261; 96/206; 96/208; 96/189; 96/214; 96/171; 96/174; 604/122

(58) Field of Classification Search
USPC .......... 95/262, 260, 261, 258; 96/206, 208, 96/189, 214, 171, 174; 604/122
See application file for complete search history.

(56) References Cited

U.S. PATENT DOCUMENTS

| | | | |
|---|---|---|---|
| 2,002,008 A | 5/1935 | Harris, Jr. | |
| 3,042,038 A | 7/1962 | Beacham | |
| 3,533,400 A | 10/1970 | Palich | |
| 3,793,805 A | 2/1974 | Hoffman | |
| 3,833,013 A * | 9/1974 | Leonard | 137/171 |
| 3,834,386 A | 9/1974 | Sisley | |
| 3,926,594 A | 12/1975 | Seib et al. | |
| 3,938,539 A | 2/1976 | Strouth et al. | |
| 3,964,479 A | 6/1976 | Boag et al. | |
| 3,976,068 A | 8/1976 | Lundquist | |
| 4,061,031 A | 12/1977 | Grimsrud | |
| 4,175,558 A | 11/1979 | Hess, III et al. | |
| 4,197,858 A | 4/1980 | Osborn | |
| 4,198,971 A | 4/1980 | Noiles | |
| 4,214,883 A * | 7/1980 | Raseley et al. | 96/189 |
| 4,304,578 A | 12/1981 | Hakala et al. | |
| 4,382,806 A | 5/1983 | Hakala et al. | |
| 4,473,478 A * | 9/1984 | Chivrall | 210/788 |
| 4,504,396 A | 3/1985 | Vardi et al. | |
| 4,559,034 A | 12/1985 | Kirita et al. | |
| 4,586,925 A | 5/1986 | Carlsson et al. | |

(Continued)

OTHER PUBLICATIONS

British Search Report dated Jan. 15, 2013.

*Primary Examiner* — Duane Smith
*Assistant Examiner* — Douglas Theisen
(74) *Attorney, Agent, or Firm* — Andrus, Sceales, Starke & Sawall, LLP

(57) ABSTRACT

A fluid trap apparatus includes an inlet configured to receive a flow of composite fluid into the apparatus. The composite fluid contains at least a first fluid and a second fluid. An outer wall defines an interior chamber. A flow diffuser is interposed within the interior chamber. The flow diffuser directs the flow of the composite fluid to circulate through the interior chamber. The first fluid and the second fluid separate as the composite fluid circulates through the interior chamber. A method of separating a first fluid from a second fluid includes introducing a flow of composite fluid into a separate chamber. A pressure gradient is created within the separation chamber. A flow diffuser is interposed in a flow path between an inlet and an outlet. The flow diffuser directs the flow of the composite fluid within the separation chamber. The first fluid and the second fluid are separated.

20 Claims, 6 Drawing Sheets

(56) References Cited

U.S. PATENT DOCUMENTS

| | | | |
|---|---|---|---|
| 4,636,196 A | 1/1987 | Tsuji et al. | |
| 4,643,713 A | 2/1987 | Viitala | |
| 4,678,460 A | 7/1987 | Rosner | |
| 4,687,495 A | 8/1987 | Maddox | |
| 4,799,374 A | 1/1989 | Bossart et al. | |
| 4,886,528 A | 12/1989 | Aaltonen et al. | |
| 4,964,984 A | 10/1990 | Reeder et al. | |
| 4,976,685 A | 12/1990 | Block, Jr. | |
| 4,985,055 A | 1/1991 | Thorne et al. | |
| 5,394,881 A | 3/1995 | Block, Jr. | |
| 5,507,858 A | 4/1996 | Jepson | |
| 5,651,765 A | 7/1997 | Haworth et al. | |
| 5,830,185 A | 11/1998 | Block, Jr. | |
| 6,053,967 A * | 4/2000 | Heilmann et al. | 96/208 |
| 6,537,356 B1 | 3/2003 | Soriano | |
| 7,279,031 B1 * | 10/2007 | Wright | 96/189 |
| 2009/0084719 A1 * | 4/2009 | Childers et al. | 210/151 |

* cited by examiner

FLUID TRAP AND METHOD OF
SEPARATING FLUIDS

BACKGROUND

The present disclosure is related to the field of medical fluid transport. More specifically, the present disclosure is related to a fluid trap for use in the delivery or removal of fluid from a patient.

When a patient is receiving extracorporeal fluid into the blood stream, exemplarily intravenous (IV) solution treatment of a transfusion of blood, there is a risk of introducing gas bubbles into the patient's vascular system. Such gas bubbles, if allowed to accumulate, can result in a gas embolism.

Additionally, many medical fluid procedures warm the blood or fluid before it is delivered to the patient as this improves patient comfort and the body's acceptance of the introduced fluid. The process of heating a fluid decreases the solubility of any gases dissolved in that fluid and therefore the warming of the blood or fluid can result in out gassing, typically of nitrogen or oxygen gas in the context of medical fluids. Therefore, it is desirable to trap and/or remove gas from a fluid before it is delivered to a patient.

BRIEF DESCRIPTION

An embodiment of a fluid trap apparatus includes an inlet configured to receive a flow of a composite fluid into the apparatus. The composite fluid contains at least a first fluid and a second fluid. A first outlet is configured to expel flow of the first fluid out of the apparatus. An outer wall is physically connected to the inlet and the outer wall defines an interior chamber. A flow diffuser is interposed within the interior chamber. The flow diffuser directs the flow of the composite fluid to circulate through the interior chamber from the inlet to the first outlet. The first fluid and the second fluid separate as the composite fluid circulates through the interior chamber.

An embodiment of a fluid trap apparatus includes an inlet configured to receive a flow of a composite fluid into the apparatus. The composite fluid includes at least a first fluid of a first density and a second fluid of a second density. A first outlet is configured to expel a flow of the first fluid out of the apparatus. An outer wall physically connects the inlet to the first outlet and the outer wall defines an interior chamber. A flow diffuser is interposed within the interior chamber in a direct flow path between the inlet and the first outlet. The flow diffuser directs the flow of composite fluid to circulate within the interior chamber between the inlet and the first outlet. The circulation of the composite fluid within the interior chamber separates the first fluid from the second fluid. A second outlet is disposed through the outer wall. The second outlet is configured to selectively remove the second fluid from within the interior chamber.

An embodiment of a method of separating a first fluid from a second fluid of a composite fluid includes introducing a flow of a composite fluid into a separation chamber through an inlet. A pressure gradient is created within the separation chamber between the inlet and a first outlet. A flow diffuser is interposed in a flow path between the inlet and the first outlet. The flow diffuser directs the flow of the composite fluid within the separation chamber. The first fluid and the second fluid are separated. The first fluid is removed from the separation chamber through the first outlet. A second outlet is selectively operated between an open configuration and a closed configuration. The second outlet is in the open configuration. The second fluid is removed from the separation chamber.

DETAILED DISCLOSURE

Figure 1:
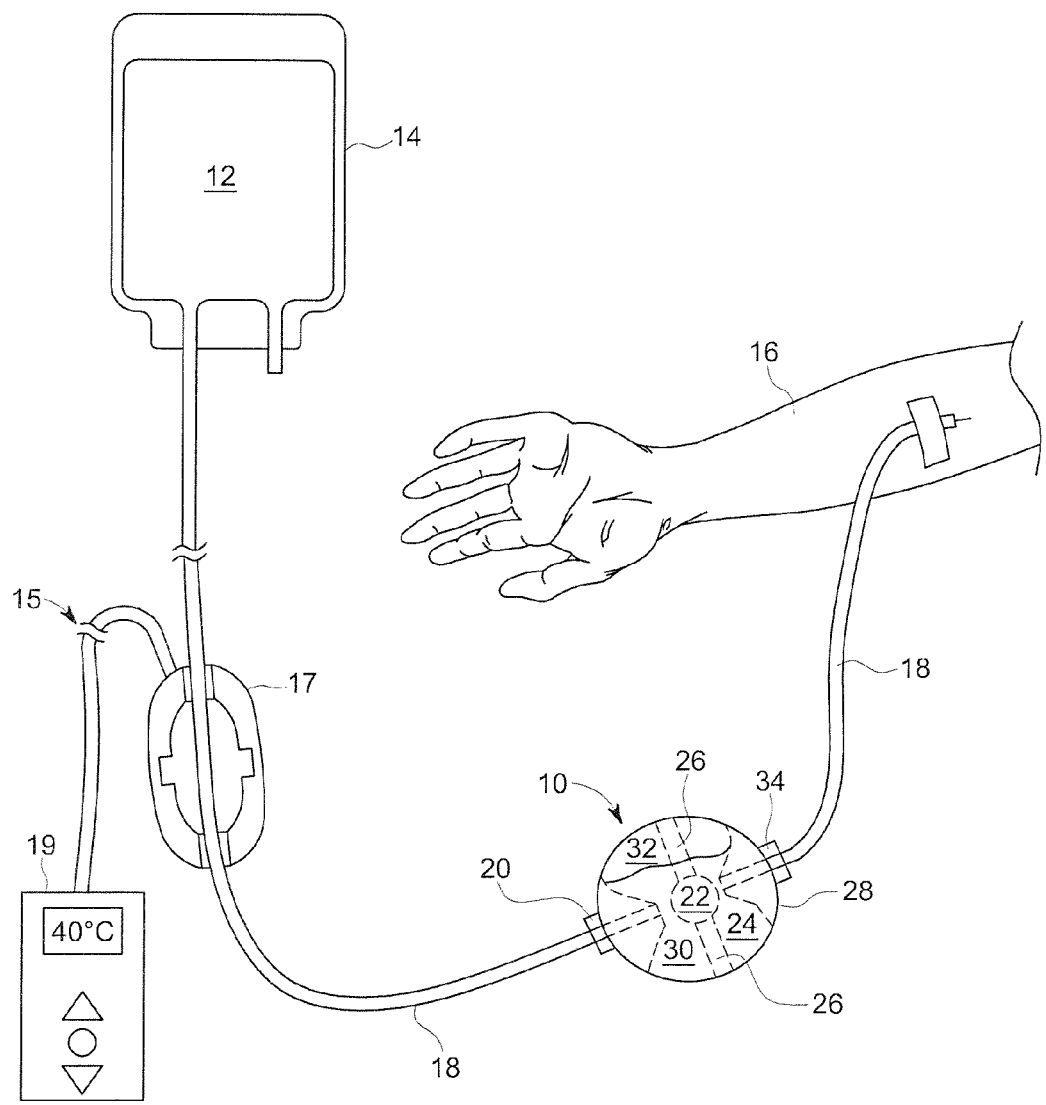
FIG. 1 is an environmental view that depicts an embodiment of a fluid trap.

FIG. 1 is an environmental view of an embodiment of a fluid trap 10 in use for the delivery of an intravenous (IV) solution 12 stored in a bag or pouch 14 to a patient 16 through a catheter 18. As will be described in further detail herein, the fluid trap 10 receives the IV solution 12 through an inlet 20. FIG. 1 further depicts an embodiment that includes a heater 15, which exemplarily may be the enFlow fluid warming system available from Vital Signs, Inc. The heater 15 exemplarily includes a warming unit 17 that secures to the catheter 18 at a position between the bag 14 and the fluid trap 10, exemplarily at a location proximal the patient 16 to minimize the distance traveled by the heated fluid. The warming unit 17 is connected to a control unit 19 which operates the warming unit 17 to a targeted warming temperature.

The IV solution 12 is a composite fluid, which is exemplarily, but not limited to, saline, medication, or blood. The IV solution 12 is a composite fluid as it is a mixture of at least two different fluids of two different densities. In many embodiments, one of the fluids is air, or another gas such as oxygen or nitrogen; however, the fluid trap 10, as disclosed herein, is not intended to be limited for use in separating air from a fluid, and may also be used in embodiments to separate one liquid from another, provided the two liquids have different densities.

When the composite fluid comprises air, or another gas, the air can be entrained in the fluid in a variety of forms. Air emboli, described above, are large bubbles of air in the fluid. Other air bubbles can be formed as a result of the heater 15, or another mechanical device through which the fluid travels before delivery to the patient. Micro bubbles are distinctly defined bubbles, but are smaller than one millimeter is diameter, and are sometimes used in contrast agent or drug delivery mechanism. Finally, air (or other gas) can be dissolved in the fluid. Changes in the physical conditions of the composite fluid (e.g. temperature, pressure, flow rate) can separate or out gas the air or other gas from the composite fluid.

The IV solution 12 enters the fluid trap 10 through the inlet 20. A diffuser 22 is supported within an open interior 24 of the fluid trap 10 by one or more supports 26 that extend inwardly from an outer wall 28 shown in FIG. 1 of the fluid trap 10. The IV solution changes paths to flow through the open interior 24 due to the positioning of the diffuser 22 within the open interior 24. The combination of the IV solution 12 striking the diffuser 22, changing direction, and circulating through the open interior 24 separates the fluid of a higher density, exemplarily saline 30, from the fluid of a lower density, exemplarily air 32. The air 32 is held within a portion of the open interior 24, while the saline 30 passes through the outlet 34 of the fluid trap 10 and is delivered to the patient 16 through the catheter 18. In this manner, the fluid trap 10 operates to prevent air bubbles that enter the fluid trap 10 through the inlet 20 from passing directly to the outlet 34.

By the shape of the fluid trap 10, with the inlet 20 and the outlet 34 aligned along a center axis of the fluid trap and the inlet 20 and the outlet 34 at least partially extending into the open interior 24, the fluid trap 10 is orientation independent so long as the trapped air 32 makes up less than a predetermined volume of the open interior. In some embodiments this predetermined volume is 20% of the volume of the open interior and in other embodiments the predetermined volume may be 30% or 40%, however, these examples of predetermined volumes are not intended to be limiting on the ranges of predetermined volumes within embodiments of the device and method as disclosed herein. Thus, as long as the volume of trapped air 32 remains below this predetermined volume, a continuous flow of separated saline 30 is provided through outlet 34. It is to be understood that while a spherical geometry of the fluid trap 10 is depicted, other geometries may be used, including, but not limited to cubic, cylinder, or conic geometries.

The fluid trap 10 represents an embodiment of a passive fluid trap that is designed as a consumable medical product. In the embodiment of the fluid trap 10, the fluid trap 10 is pre-primed, exemplarily during production of the fluid trap 10 or by gravity or syringe priming, to be filled with fluid, such as saline 30. As air is trapped, an increasing volume of air 32 displaces volume of saline 30. As there is no mechanism for the release of the trapped air 32, the fluid trap 10 must be monitored by a clinician such that the fluid trap 10 is replaced before the volume of trapped air 32 becomes so much as to reach the outlet 34 and be delivered to the patient.

Figure 2:
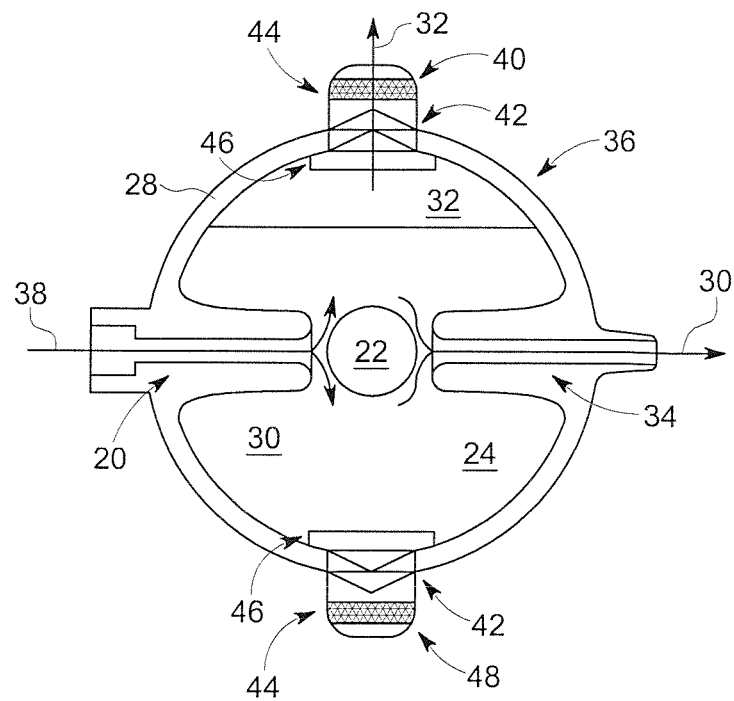
FIG. 2 depicts an embodiment of a passive fluid trap.

FIG. 2 is an alternative embodiment of a passive fluid trap 36. It should be noted that throughout the exemplarily embodiments disclosed herein, like reference numerals are used to described like structures between the embodiments.

The fluid trap 36 receives the flow of composite fluid 38, which in the present example is a combination of saline and air, through the inlet 20. As the composite fluid 38 flows into the open interior 24 of the fluid trap 36, the flow of composite fluid 38 is dispersed by the diffuser 22. In the fluid trap 36, the diffuser 22 is located adjacent the inlet 20 such that the diffuser 22 causes a change in the direction of the flow of the composite fluid 38 upon the composite fluid 38 entering the open interior 24, although it will be recognized that alternative embodiments may include alternative relationships between the inlet 20 and the diffuser 22. As depicted in FIG. 2, the inlet 20 extends towards the center of the open interior 24 where the diffuser 22 is located. The dispersion of the composite fluid 38 caused by the diffuser 22 causes the composite fluid 38 to circulate within the open interior 24 causing separation of the air 32 from the saline 30. As the saline 30 is of a lower density than the air 32, saline 30 separates to a bottom portion of the fluid trap 36 due to gravity. In embodiments of the fluid trap 36, the fluid trap 36 is primed at the start of use by filling the open interior with either the composite fluid 38, or saline 30. As the fluid trap 36 is used and the air 32 collects within the open interior 24, the volume of the open interior 24 that retains the air 32 increases, so long as such volume of air 32 is retained at a predetermined volume, exemplarily at a percentage less than 50% of the total volume of the open interior 24, in alternative embodiments 40%, or any alternative volume as may be recognized by one of ordinary skill in the art, the separated saline 30 will continue to flow from the open interior 24 out through outlet 34. As depicted in FIG. 2, the outlet 34 extends into the open interior 24 towards the diffuser 22.

In alternative embodiments, and as disclosed in further detail herein, one or both of the inlet 20 or outlet 34 may comprise helical grooves or ridges (not depicted). Changes in the composite fluid 38 flow rate or direction can facilitate separation of the fluids. A helical geometry in one or both of these structures can create a centrifugal force that separates the first and second fluids. In still further embodiments disclosed herein, the geometry within the open interior 24 is modified, exemplarily with a helical flow path (not depicted) to control the flow of the composite fluid. In one embodiment, such a geometry can have the effect of reducing turbulence to keep unnecessary air from being removed from solution in the composite fluid. Further, such an embodiment may reduce sheer stresses within the fluid trap that can contribute to hemolysis when the composite fluid comprises blood.

In embodiments of the fluid trap 36, the fluid trap 36 is primed at the start of use by filling the open interior with either the composite fluid 38, or saline 30. The fluid trap 10 can be primed by a clinician using a syringe to either inject or aspirate fluid within the fluid trap 10. As the fluid trap 36 is used and the air 32 collects within the open interior 24, the volume of the open interior 24 that retains the air 32 increases, so long as such volume of air 32 is retained at a predetermined volume. Exemplarily, the predetermined volume is a percentage less than 45% of the total volume of the open interior 24, in alternative embodiments 40%, or any alternative volume as may be recognized by one of ordinary skill in the art, the separated saline 30 will continue to flow from the open interior 24 out through outlet 34. Functionally, the predetermined volume is a volume of air 32 (or other trapped fluid) that the fluid trap 36 can maintain trapped within passing the air 32 (or other trapped fluid) through the outlet 34, independent of the orientation of the fluid trap 36.

In the fluid trap 36, the diffuser 22 is spherical in shape; however, the diffuser 22 can be of a variety of other shapes, as disclosed herein. Additionally, the diffuser 22 can be configured at the center of the fluid trap 36, or may be offset in the direction of one or the other of the inlet 20 and outlet 34.

The fluid trap 36 is designed to passively control the volume of air 32 retained within the open interior 24 through an outlet 40. The outlet 40 is designed to facilitate the passive release of the air 32 from the open interior 24. The outlet 40 includes a pressure release valve 42 that is designed to open upon a predetermined pressure to release the air 32. The pressure release valve 42 may be any of a variety of one-way or check valves designed to open upon a predetermined pressure. Non-limiting examples of such valves include ball valves, pop off valves, or umbrella valves. In still further embodiments, a combination of two or more valves provides redundancy or multiple valves in series or parallel can be directed to specific functions (e.g. retaining blood within the fluid trap or passing air out of the fluid trap).

A filter 44 is retained within the outlet 40 downstream of the pressure release valve 42 to retain any residual substance entrained in the air 32 that is expunged through the outlet 40. In examples wherein the composite fluid 38 is of a biological or medicinal substance, it may be desirable to prevent the release of any of these fluids that may be saturated in the air 32 that is released into the external environment. Therefore, the filter 44 may be selected such as to remove any such material before the air 32 is released. Non-limiting examples of the filter 44 can be hydrophopic membranes of hydrophilic membranes.

Additionally, some embodiments may include a selectively permeable membrane 46 that is permeable to the second fluid, to be removed with the fluid trap 36, yet the selectively permeable membrane 46 is impermeable to the denser fluid to be released through the outlet 34. The addition of the selectively permeable member 46 further helps to ensure that only the air 32 is released through the outlet 40.

In the exemplary embodiment of the fluid trap 36, multiple outlets 40 are located around the perimeter of the outer wall 28. Outlet 48 is located 180° away from the outlet 40 around the fluid trap 36. However, it will be recognized that alternative embodiments may locate the outlets in any of a variety of orientations with respect to the other outlets. Therefore, the selectively permeable membrane 46 of the outlet 48 keeps the saline 30 from being released through the outlet 48. The inclusion of multiple outlets 40, 48 around the perimeter of the fluid trap 36 make the fluid trap 36 position-independent in that regardless of an orientation, the air 32 can be released through an outlet 40, 48, preserving flow of the saline 30 out of the outlet 34. In further embodiments, the outlet 40 extends along an entire circumference around the fluid trap 36. In still further embodiments, multiple outlets 40 are spaced across the entire surface of the fluid trap 36.

The outlet 34 may be dimensioned to be a smaller diameter than the inlet 20. Alternatively, the inlet 20 may be dimensioned to be a smaller diameter than the outlet 34. Either of these configurations can create a pressure gradient across the open interior 24 of the fluid trap 36. This pressure gradient facilitates the expulsion of the air 32 through the pressure release valve 42 of an outlet 40, 48. In still further embodiments, the outlet 34 has an adjustable orifice (not depicted), or can be selectively or partially occluded. In some embodiments, one or more of the outlets 40 can extend through the outer wall 28 at the outlet 34. Such an embodiment can be an outlet such as an umbrella valve that is configured circumferentially about the outlet 34. While not depicted, these embodiments may further provide any last removal of separated air 32 before the saline 30 leaves the fluid trap, or to remove any separated air 32 that is removed by helical grooves or ridges (not depicted) located in the outlet 34 as described above.

In some embodiments, maintenance of volumetric flow through the fluid trap 36 is desired while a change to another environmental condition within the fluid trap 36 is created, exemplarily, but not limited to, pressure, flow rate, or internal geometry in order to create a Venturi effect within the fluid trap 36.

Figure 3:
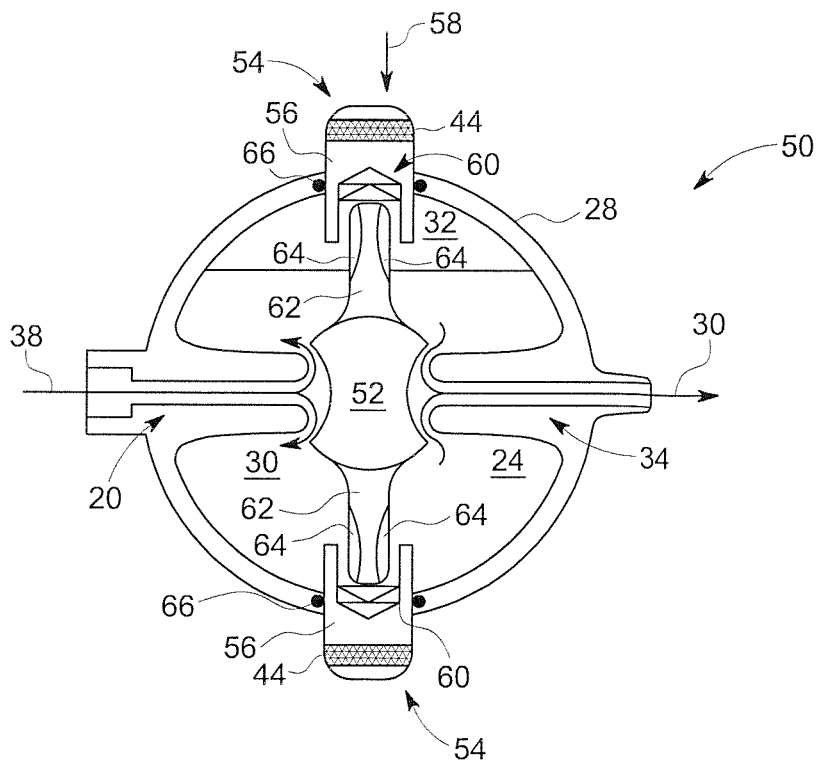
FIG. 3 depicts an embodiment of a fluid trap with a manually operated outlet.

FIG. 3 depicts an embodiment of an actively operated fluid trap 50. As described above, a flow of composite fluid 38 is received into the fluid trap 50 through an inlet 20. The fluid trap 50 exemplarily includes an alternative embodiment of a diffuser 52. The diffuser 52 is shaped to create increased dispersion of the composite fluid 38 upon entry into the open interior 24 by at least partially surrounding the inlet 20. The increased dispersion and change of direction in the flow path of the composite fluid 38 facilitates the separation of the air 32 from the saline 30. As in other embodiments, the air 32 and the saline 30 are collected within the fluid trap 50 based upon gravity. The saline 30 is expelled from the fluid trap 50 through the outlet 34 after the diffuser 52 causes further changes in the flow path of the saline 30 by at least partially surrounding the outlet 34.

The fluid trap 50 provides an example of an active outlet 54 which must be actuated, such as by a clinician or automated, in order to release the air 32 from the open interior 24 of the fluid trap 50. The outlet 54 includes a movable actuator 56 that upon receiving a force in the direction of arrow 58 moves in the same direction into the open interior 24. This movement engages a valve 60 with a post 62 that opens the valve 60 to release the air 32 therethrough. The post 62 is configured, exemplarily with release passages 64 to provide a passageway for the release of the air 32 through the open valve 60. However, it is to be recognized that alternative geometries or configurations may be used to achieve similar purposes, exemplarily, but not limiting, the release passages could be ports, grooves, or channels.

The actuator 56 is biased in the closed or outwardly extending position in any one of a variety of known biasing techniques, including springs material deformation, or geometrically created biasing techniques, such that upon release of pressure in the direction of arrow 58, the actuator 56 returns to its fully extended position, closing the valve 60. Seal 66, which is exemplarily an O-ring, provides a fluid seal about the actuator 56 across the outer wall 28.

Figure 4A:
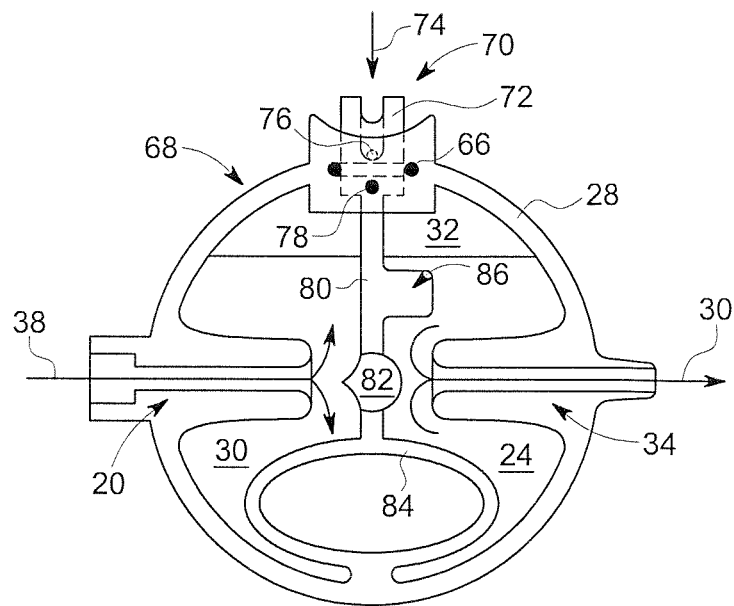
FIGS. 4A and 4B depict the operation of an alternative embodiment of a fluid trap.
Figure 4B:
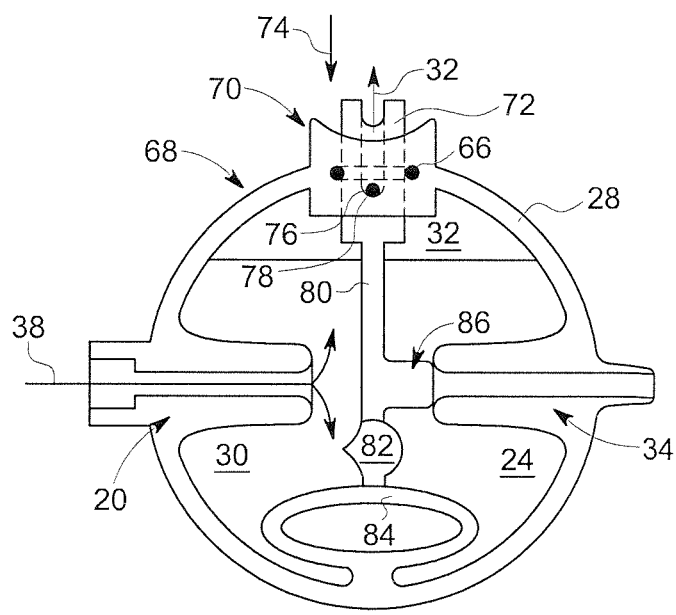

FIGS. 4A and 4B depict an alternative embodiment of an actively operated fluid trap 68. FIG. 4A depicts the fluid trap 68 in a closed configuration in which the air 32 is collected within the open interior 24 of the fluid trap 68 while the saline 30 is directed out through the outlet 34. FIG. 4B depicts an open configuration wherein the air 32 is expelled from the open interior 24 through an outlet 70 and the outlet 34 is at least partially occluded from flow of saline 30.

The outlet 70 includes an actuator 72 that is operable by a clinician by pressing the actuator 72 in the direction of arrow 74. The operation of the actuator 72 switches the fluid trap 68 between the open and closed configurations. The actuator 72 includes an outlet port 76 and a seal 66 maintains a fluid seal between the outer wall 28 and the actuator 72.

The outer wall 28 further includes a fluid port 78. When the fluid trap 68 is in the closed configuration, as depicted in FIG. 4A, the outlet port 76 of the actuator 72 is out of alignment with the fluid port 78 of the outer wall 28 and the seal 66 provides a fluid seal preventing any fluid flow between the fluid port 78 and outlet port 76. In one embodiment a membrane (not depicted) in the actuator 72 provides further protection against overflow or release of the saline 30 through the outlet port 76. In a still further embodiment, the actuator 72 includes threads (not depicted) such as to engagingly receive a syringe which is used to draw the air out through the outlet port 76 of the actuated actuator 72 in a controlled and confined manner.

The actuator 72 further includes a shaft 80 that extends into the open interior 24 of the fluid trap 68 and is connected to the diffuser 82. The shaft 80 locates the diffuser 82 in a position adjacent the inlet 20 and the outlet 34, such that the diffuser 82 is interposed in a direct flow path therebetween, when the fluid trap 68 is in the closed configuration based upon the position of the actuator 72.

Diffuser 82 provides an exemplary alternative of an embodiment of a diffuser. It is to be recognized that the diffuser 82 could be used in a variety of embodiments disclosed herein, while the fluid trap 68 may use a variety of diffusers.

Biasing element 84, which may be a spring (not depicted) or, as depicted, a deformable structural component, biases the actuator 72 against a force in the direction of arrow 74. Thus, the fluid trap 68 is biased to the closed configuration.

As will be described in further detail herein, a stopper 86 extends from the shaft 80 in a direction of the outlet 34. When the actuator 72 is in the closed configuration, the stopper 86 extends into the open interior 24, but does not substantially impede the flow of saline 30 out of the fluid trap 68 through the outlet 34.

The actuator 72 depicts one exemplary embodiment of the actuators that may be used in embodiments of the fluid trap 68. In an alternative embodiment, the actuator further includes helical tracks such that the actuator rotates as it is pressed, rotating the stopper across the outlet. In another embodiment, rather than being pressed, the actuator 72 is rotated about an axis to move the fluid trap 68 between the open and closed configurations. In such an embodiment, the actuator 72 can maintain alignment of the diffuser 82 with the inlet 20 while moving the stopper 86 across the outlet 34, occluding the outlet 34.

FIG. 4B depicts the fluid trap 68 in the open configuration, which is created by a force applied to the actuator 72 in the direction of arrow 74. The force in the direction of arrow 74 overcomes the biasing force provided by the biasing element 84, compresses the biasing element 84, and the actuator 72 moves in the direction of arrow 74 into the open interior 24 of the fluid trap 68. The movement of the actuator 72 aligns the outlet port 76 of the actuator 72 with the fluid port 78 of the outer wall 28 and thus the air 32 travels through the aligned fluid port 78 and outlet port 76 from the open interior 24 to the exterior of the fluid trap 68.

Simultaneously with the alignment of the fluid port 78 and the outlet port 76, the stopper 86 is moved in the direction of arrow 74 into a position that substantially impedes the flow of the saline 30 out of the fluid trap 68 through the outlet 34. By blocking the outlet 34 with the stopper 86 while the combined fluid 38 is still entering the fluid trap 68 through the inlet 20, the pressure within the open interior 24 will increase, thus further forcing the air 32 out of the outlet 70 through the aligned fluid port 78 and outlet port 76. The increase in fluid pressure helps to facilitate the expelling of the air 32 from the fluid trap 68. It is to be understood that, in an embodiment, the stopper 86 can occlude or partially occlude the outlet 34. In an alternative embodiment, the stopper changes another environmental condition within the fluid trap 68 such as, but not limited to, the flow rate of the saline 30 or the flow path of the saline 30.

When the air 32 has been expelled through the outlet 70, the clinician can end the expelling of the air 32 by releasing the force on the actuator 72 in the direction of arrow 74 and the biasing element 84 moves the actuator 72 and returns the fluid trap 68 to the closed configuration. Air 32 will once again build up within the open interior 24 of the fluid trap 68, now in the closed configuration.

Figure 5A:
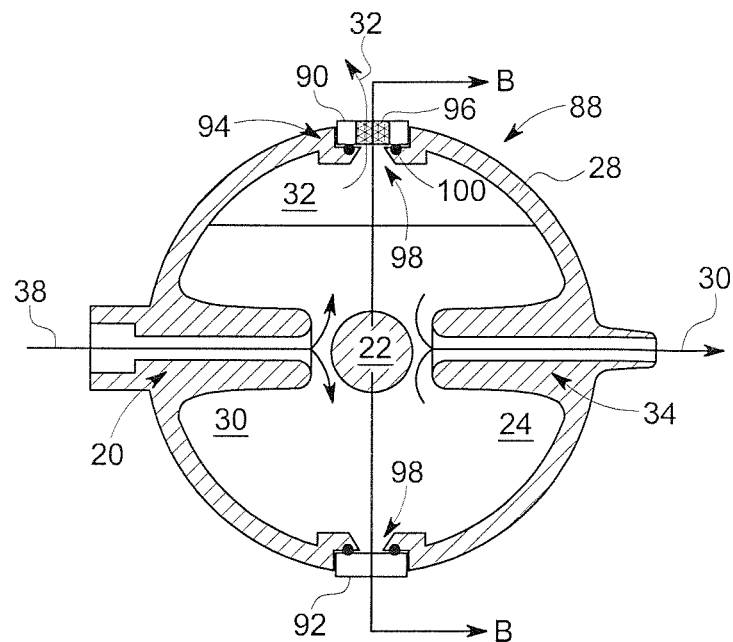
FIGS. 5A and 5B depict an alternative embodiment of an outlet arrangement for a fluid trap.
Figure 5B:
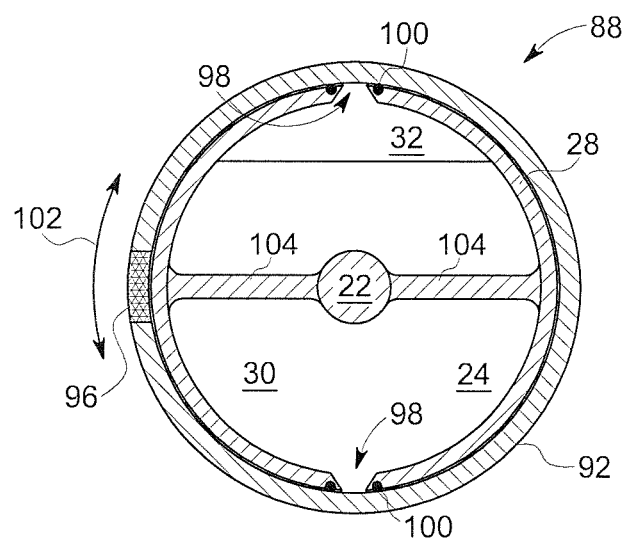

FIGS. 5A and 5B depict a still further embodiment of an actively operated fluid trap 88. FIG. 5A is a cutaway view of the fluid trap 88 along a plane coincident with the flow path of the composite fluid 38 and saline 30 between the inlet 20 and the outlet 34. FIG. 5B is a cutaway view along a plane identified as line B-B in FIG. 5A that is perpendicular to the flow between the inlet 20 and the outlet 34.

The fluid trap 88 includes a rotatably actuated valve 90 that includes a rotatable ring 92 that rotates within a recessed track 94 (or other engagement) of the outer wall 28. The rotatable ring 92 includes an outlet 96 that may include a filter or other selectively permeable membrane, as disclosed above, through which the air 32 from the open interior 24 can pass. The ring 92 is rotatable within the recessed track 94 such as to selectively align the outlet 96 in the ring 92 with a fluid port 98 through the outer wall 28. A seal 100, which is exemplarily an O-ring, but would be recognized by one of ordinary skill in the art to be any of a variety of suitable seals for use in the presently disclosed embodiment, maintains a fluid seal between the outer wall 28 within the recessed track 94 and the rotatable ring 92.

FIG. 5A depicts the fluid trap 88 in an open configuration such that the outlet 96 is aligned with the fluid port 98, and the air 32 passes through the fluid port 98 and the outlet 96 exterior of the fluid trap 88.

As shown in FIG. 5B, the rotatable ring 92 is rotatable within the recessed track 94 about the fluid trap 88 in the direction of arrow 102. By rotating the rotatable ring 92 to a position wherein the outlet 96 is out of alignment with the fluid port 98, the fluid trap 88 is placed in a closed configuration and the air 32 is permitted to build up within the open interior 24 of the fluid trap 88. As further shown in FIG. 5B, one or more supports 104 may extend from the outer wall 28 of the fluid trap 88, wherein the supports 104 hold the diffuser 22 in a specified alignment between the inlet 20 and the outlet 34.

Figure 6A:
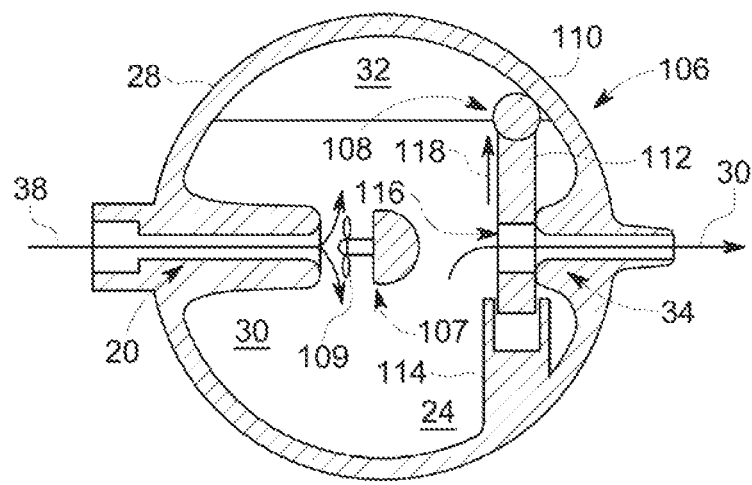
FIGS. 6A and 6B depict an embodiment of a fluid trap with an outlet seal.
Figure 6B:
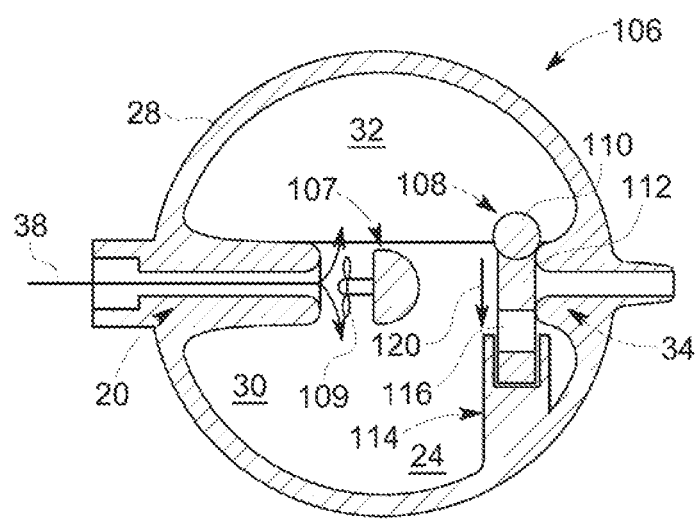

FIGS. 6A and 6B further depict an alternative embodiment of a passive fluid trap 106. It is to be understood, however, that embodiments of the fluid trap 106 may be designed as an active fluid trap by implementing any of the outlets as disclosed above in the previous embodiments. Additionally, a still further embodiment of an active fluid trap may be implemented with the use of a threaded outlet connection (not depicted), such as a Luer-Lok™. In such an embodiment, a threaded male or female connection is provided through the outer wall 28 and a clinician or technician can remove air 32 from the fluid trap 106 with the use of a syringe with an appropriate mating threaded connection.

The fluid trap 106 depicts a still further embodiment of a diffuser 107 that can be implemented in fluid traps disclosed herein. The diffuser 107 includes a fan blade 109 that rotates as the composite fluid 38 flows into the fluid trap 106 through inlet 20. The diffuser 107 represents a mechanical design of a diffuser that causes further agitation of the composite fluid, facilitation separation into the first fluid and the second fluid.

Returning to the embodiment of the fluid trap 106 depicted in FIGS. 6A and 6B, the fluid trap 106 includes an outlet seal 108. The outlet seal 108 includes a float 110. The float 110 is designed to be buoyed by the fluid of the composite fluid 38 that is of a greater density, exemplarily saline 30. The float 110, as depicted in FIGS. 6A and 6B, therefore is suspended at the interface between the air 32 and the saline 30. A stem 112 extends from the float 110 and travels within a recess 114. The stem 112 includes an opening 116, such that when the outlet seal 108 is buoyed in the direction of arrow 118, the opening 116 is substantially aligned with the outlet 34 and the saline 30 can exit the fluid trap 106 through the outlet 34. In an alternative embodiment (not depicted), the float 110 also operates as the outlet seal, limiting or blocking air from entering the outlet as the trapped air building up within the fluid trap as disclosed herein.

It is to be understood that in embodiments, the outlet seal 108 and float 110 can be configured to be freely rotatable about a central axis. In still further embodiments, the outlet seal 108 and float 110 are movably held within the recess 114, or another similar recess (not depicted) such as to operate independently from the orientation of the fluid trap 106. In one merely exemplary embodiment, such outlet seal (not depicted) may position the float in the middle of the outlet seal with two or more openings (not depicted) configured in the outlet seal for operation connection with various fluid trap orientations. In a still further embodiment, the float itself is dimensioned to operate as the outlet seal, facilitating occlusion or partial occlusion of the outlet.

However, as the air 32 builds up within the open interior 24 of the fluid trap 106, the outlet seal 108 moves in the direction of arrow 120 and the opening 116 is moved into recess 114 and the stem 112 substantially blocks the outlet 34 from expelling a flow of saline 30, as depicted in FIG. 6B. Since the flow of composite fluid 38 is continuously provided to the fluid trap 106, the pressure within the fluid trap 106 may further increase such as to compress the volume taken up by the air 32 within the open interior 24 such that the outlet seal 108 moves in the direction of arrow 118 sufficiently enough so as to again permit the exiting flow of the saline 30. In any event, the outlet seal 108 mechanism provides a safety feature against a critical volume of air 32 being trapped within the open interior 24, thus prevents the inadvertent delivery of air 32 to the patient.

Embodiments of the fluid trap, as described above, can gradually create a pressure gradient within the fluid trap by progressively restricting flow out of the outlet as the air builds up within the air trap. This buildup of air forces the float to occlude the outlet.

As noted above, the embodiment of the fluid trap 106 may be implemented as an actively operated fluid trap from which the air 32 can be removed, by the addition one of the above-described outlets. In such embodiments of the fluid trap 106 configured to passively or actively expel the trapped air 32, the blocking of the outlet 34 by the outlet seal 108 can increase the pressure within the open interior, thus facilitating the removal of the trapped air 32.

Figure 7:
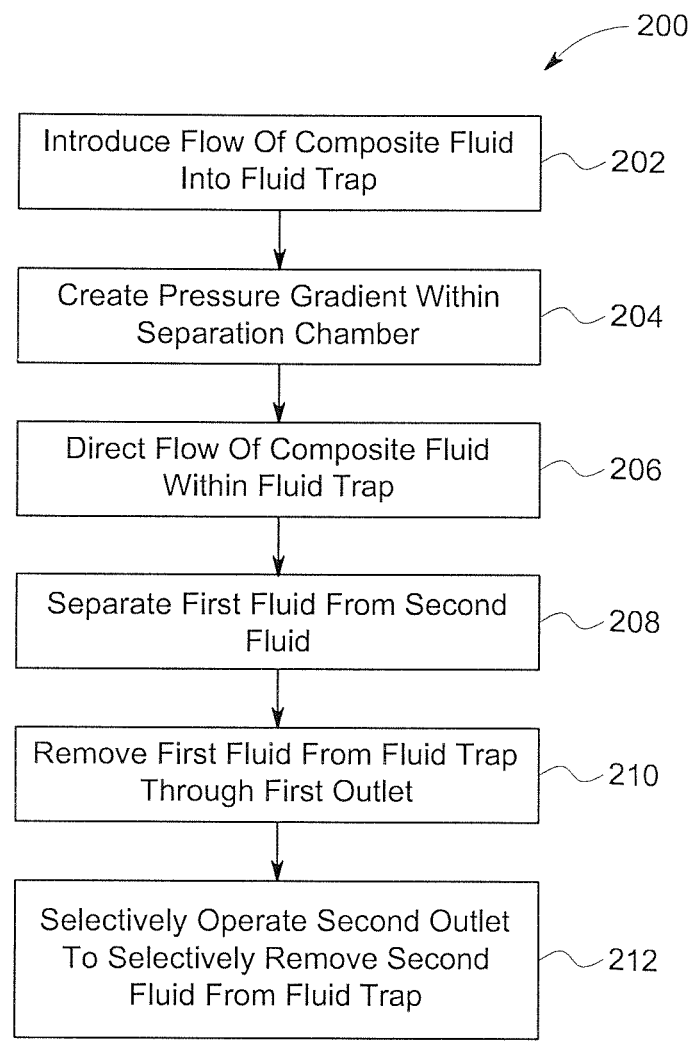
FIG. 7 is a flow chart that depicts an embodiment of a method of separating a first fluid from a second fluid.

FIG. 7 is a flow chart that depicts an embodiment of a method of separating a first fluid from a second fluid of a composite fluid. It is to be understood that the method 200 as depicted in FIG. 7 may be implemented in a variety of ways including some or all of the actions shown in method 200. Additionally, it will be recognized by one of ordinary skill that within the scope of the present disclosure, certain disclosed features of the method 200 may be performed in alternative orders than that specifically disclosed in the flow chart of method 200 while being within the scope of the present disclosure.

At 202, the method 200 begins with the introduction of a flow of composite fluid into the fluid trap. As disclosed above, the composite fluid is a fluid that includes a first fluid of a first density and a second fluid of a second density. In some embodiments, the first fluid and the second fluid may both be liquids, while in other embodiments, the first fluid and the second fluid may be a liquid and a gas, respectively. The introduction of the flow of composite fluid into the fluid trap at 202 may further constitute the act of priming the fluid trap such that the flow of composite fluid is provided while the fluid trap is operated in an open configuration, such that the second outlet, as described above, is opened to expel any gas from the open interior 24 which otherwise may be referred to as a separation chamber. The act of priming the fluid trap will thus remove any residual gas such that a maximum amount of the second fluid may be accumulated in the fluid trap before replacement of the fluid trap or, alternatively, expelling the accumulated second fluid from the fluid trap as required. In still further embodiments, the fluid trap may be provided pre-primed, exemplarily with an inert liquid such as saline, so that a clinician or technician need not manually prime the fluid trap before use.

At 204, a pressure gradient is created within the separation chamber of the fluid trap. A pressure gradient can be created or established in a variety of manners as disclosed above. Exemplary techniques for creating the pressure gradient include differing dimensions between the inlet and the outlet of the fluid trap or the operation of a flow restrictor, such as an outlet seal, to at least partially occlude an outlet from the fluid trap.

The flow of the composite fluid is directed within the fluid trap at 206. The composite fluid is received by the fluid trap through an inlet and is directed to circulate through the separation chamber, such as through the use of a diffuser that is positioned in relation to at least the inlet or the outlet of the fluid trap.

Next, at 208, the first fluid is separated from the second fluid of the composite fluid. As disclosed above, the circulation of the composite fluid within the separation chamber facilitates the separation of the first fluid and the second fluid through the force of gravity based upon the respective different densities of the first fluid and the second fluid.

As detailed above, impact or other mechanical forces, pressure drop, changes in flow rate, or other environmental conditions within the fluid trap can also be used to separate the first and second fluids.

At 210, the first fluid is removed from the fluid trap through a first outlet. In embodiments, differences between the diameters of the inlet and the outlet can create pressure gradients within embodiments of the fluid traps disclosed herein. In still further embodiments, a stopper, actuator, or other type of flow restrictor, such as a valve, controls the flow of the first fluid out of the first outlet. This can cause the pressure gradient or other environmental change in the fluid trap that facilitates separation and removal of the second fluid.

At 212, a second outlet is selectively operated to selectively remove the second fluid from the fluid trap. As disclosed above, the second outlet is configured, such that the separated second fluid accumulates about the second outlet and the selective operation of the second outlet removes the accumulated second fluid from the fluid trap. As disclosed above, a variety of outlets may be used as the second outlet while remaining within the scope of the current disclosure. A non-limiting list of such exemplary outlets include passively operated pressure valves, actively operated push valves, or a rotatably operated valve.

The current disclosure has primarily relied upon an exemplary description of a composite fluid that comprises saline and air as the first and second fluids. However, it will be recognized that is not intended to be limiting on the scope of situations or composite fluids with which the presently disclosed embodiments of fluid traps may be used. In an alternative embodiment, the composite fluid can be blood provided to the patient as part of a blood transfusion. The blood may exemplarily be circulated through a warmer (not depicted) such as to elevate the temperature of the blood to an approximate internal temperature of the patient. The warming of the blood may reduce the solubility of gas dissolved within the blood, particularly oxygen and/or nitrogen, and the fluid trap may operate to remove any accumulation of out gassed oxygen, nitrogen, or other gases in the blood before the blood is delivered to the patient.

A variety of exemplary embodiments of the fluid trap have herein been disclosed. It is to be understood that further combinations of the components disclosed herein (e.g. combinations of inlets, diffusers, and first and second outlets) are within the scope of the disclosure, as would be recognized by one of ordinary skill in the art.

In still further embodiments, the fluid trap may be connected within a breathing circuit of a patient receiving mechanical ventilation support. In such an embodiment, the fluid trap operates to collect and expel moisture and/or mucus from the breathing circuit in order to prevent the recirculation of these substances back to the lungs of the patient. As would be recognized by one of ordinary skill in the art, the composite fluid in these embodiments would be an exhaled breath of air from the patient within which water vapor and mucus is entrained. In these embodiments, the fluid trap operates to separate and retain the more dense fluid (e.g. condensed water or mucus) while facilitating the flow of the less dense fluid (e.g. air) through the fluid trap between the inlet and the outlet.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A fluid trap apparatus comprising:
    an inlet configured to receive a flow of a composite fluid into the apparatus, the composite fluid having at least a first fluid and a second fluid;
    an outer wall physically connected to the inlet, the outer wall defining an interior chamber;
    a flow diffuser interposed within the interior chamber, the flow diffuser directs the flow of the composite fluid to circulate through the interior chamber, wherein the first fluid and the second fluid separate as the composite fluid circulates through the interior chamber;
    a first outlet physically connected to the outer wall, the first outlet configured to expel a flow of the separated first fluid out of the apparatus; and
    a second outlet disposed through the outer wall and configured to expel a flow of the separated second fluid out of the apparatus, wherein the separated second fluid aggregates about the second outlet, and the second outlet is operable between a first configuration to retain the separated second fluid within the interior chamber and a second configuration to expel the separated second fluid.

2. The fluid trap of claim 1, further comprising a flow restrictor in fluid communication with the first outlet and the flow restrictor is operable to at least partially occlude the first outlet and the at least partial occlusion of the first outlet creates a pressure gradient between the inlet and the first outlet that forces the second fluid out of the second outlet when the second outlet is in the second configuration.

3. The fluid trap of claim 1, wherein the inlet has an interior diameter that is larger than an interim diameter of the first outlet that creates a pressure gradient between the inlet and the first outlet which forces the second fluid out of the second outlet when the second outlet is in the second configuration.

4. The fluid trap of claim 1, further comprising a manually actionable valve in the second outlet, the valve being selectively operable to place the second outlet in the first configuration and the second configuration.

5. The fluid trap of claim 4, further comprising a membrane, wherein the membrane is permeable to the second fluid and the membrane retains the first fluid about the second outlet.

6. The fluid trap of claim 4, wherein the inlet has an interior diameter that is larger than an interior diameter of the first outlet which creates a pressure gradient between the inlet and the first outlet which forces the second fluid out of the second outlet when the second outlet is in the second configuration.

7. The fluid trap of claim 1 wherein the flow diffuser is further adjacent the first outlet such that the flow of the first fluid changes direction prior to exiting through the first outlet.

8. The fluid trap of claim 7, wherein the flow diffuser is further adjacent the inlet such that the flow of the composite fluid changes direction upon entering the interior chamber.

9. The fluid trap of claim 8, wherein the inlet and the first outlet each extend towards an interior of the interior chamber, and the flow diffuser is located at the center of the interior chamber, such that the first fluid circulates in the interior chamber around the flow diffuser.

10. The fluid trap of claim 9, wherein the flow diffuser at least partially surrounds the inlet and the first outlet.

11. A method of separating a first fluid from a second fluid of a composite fluid, the method comprising:
    introducing a flow of the composite fluid into a separation chamber through an inlet, the separating chamber having a first outlet;
    creating a pressure gradient within the separation chamber between the inlet and the first outlet;
    interposing a flow diffuser in a flow path between the inlet and the first outlet, the flow diffuser directing the flow of the composite fluid within the separation chamber;
    separating the first fluid and the second fluid based upon the first density and the second density;
    removing the first fluid from the separation chamber through the first outlet; and
    selectively operating a second outlet between an open configuration and a closed configuration, wherein the second fluid is removed from the separation chamber when the second outlet is in the open configuration.

12. The method of claim 11, further comprising:
    establishing a pressure gradient between the inlet and the first outlet; and
    removing the second fluid through the second outlet due to the pressure gradient.

13. The method of claim 12, further comprising operating a flow restrictor connected to the first outlet to create the pressure gradient between the inlet and the first outlet.

14. The method of claim 13, wherein operating the second out open configuration at least partially occludes the first outlet.

15. The method of claim 14, wherein the second outlet is a valve.

16. The method of claim 12, wherein the second outlet further comprises a manually actionable valve, and further comprising actuating the valve to place the second outlet in the open configuration.

17. A fluid trap apparatus comprising:
    an inlet configured to receive a flow of a composite fluid into the apparatus, the composite fluid having at least a first fluid and a second fluid;
    an outer wall physically connected to the inlet, the outer wall defining an interior chamber;
    a flow diffuser interposed within the interior chamber, the flow diffuser directs the flow of the composite fluid to circulate through the interior chamber, wherein the first fluid and the second fluid separate as the composite fluid circulates through the interior chamber;
    a first outlet physically connected to the outer wall, the first outlet configured to expel a flow of the separated first fluid out of the apparatus; and
    a second outlet disposed through the outer wall and configured to expel a flow of the separated second fluid out of the apparatus, wherein the separated second fluid aggregates about the second outlet, and the second outlet is operable between a first configuration to retain the separated second fluid within the open interior and a second configuration to expel the separated second fluid wherein the second outlet cooperates with the first outlet such that operation of the second outlet to the second configuration to expel the second fluid also at least partially occludes the first outlet and a pressure gradient between the inlet and the first outlet forces the second fluid out of the second outlet when the second outlet is in the second configuration.

18. The fluid trap of claim 17, further comprising:
a valve in the second outlet, the valve being operable to place the second outlet in the first configuration and the second configuration; and
a membrane in the second outlet, wherein the membrane is permeable to the second fluid and the membrane retains the first fluid about the second outlet.

19. The fluid trap of claim 17, wherein the flow diffuser is positioned adjacent the inlet and the first outlet.

20. The fluid trap of claim 19, wherein the flow diffuser at least partially surrounds the inlet and the first outlet.

* * * * *